US00PP36087P2

(12) United States Plant Patent
Lim

(10) Patent No.: US PP36,087 P2
(45) Date of Patent: Sep. 3, 2024

(54) FLORIBUNDA SHRUB ROSE PLANT NAMED 'LIMteatime'

(50) Latin Name: *Rosa hybrida*
Varietal Denomination: LIMteatime

(71) Applicant: Altman Specialty Plants Inc., Vista, CA (US)

(72) Inventor: Peter Lim, Escondido, CA (US)

(73) Assignee: Altman Specialty Plants Inc, Vista, CA (US)

( * ) Notice: Subject to any disclaimer, the term of this patent is extended or adjusted under 35 U.S.C. 154(b) by 0 days.

(21) Appl. No.: 18/371,523

(22) Filed: Sep. 22, 2023

(51) Int. Cl.
*A01H 5/02* (2018.01)
*A01H 6/74* (2018.01)

(52) U.S. Cl.
USPC ..... Plt./148
CPC ..... *A01H 6/749* (2018.05)

(58) Field of Classification Search
USPC ..... Plt./148
CPC ..... A01H 6/749; A01H 5/02
See application file for complete search history.

*Primary Examiner* — Keith O. Robinson
(74) *Attorney, Agent, or Firm* — Cassandra Bright

(57) ABSTRACT

A new and distinct miniature shrub multiflora Rose plant named 'LIMteatime' is disclosed, characterized by distinctive fully double pink flowers with a strong, lemony, tea rose fragrance. Plants are vigorous and can be grown on their own roots. Plants are semi-upright, spreading, and exhibit good resistance to blackspot diseases. The new variety is normally produced as an outdoor garden or container plant.

1 Drawing Sheet

Latin name of the genus and species: *Rosa hybrida.*
Variety denomination: 'LIMteatime'.

BACKGROUND OF THE INVENTION

The new *Rosa* cultivar is a product of a planned breeding program conducted by the inventor, Peter Lim. The objective of the breeding program was to produce new garden rose varieties with continuous blooming for ornamental commercial applications. The cross resulting in this new variety was made at a nursery in McMinnville, Oregon, in June of 2009.

The seed parent is an unnamed, unpatented *Rosa* seedling. The pollen parent is the variety *Rosa* 'BAIgirl', U.S. Plant Pat. No. 19,952. The new variety was selected in July of 2010 by the inventor at the same nursery in McMinnville, Oregon.

Asexual reproduction of the new cultivar has been performed by vegetative cuttings. This was first performed at a research greenhouse in McMinnville, Oregon, in July of 2010 and has shown that the unique features of this cultivar are stable and reproduced true to type in more than 5 successive generations.

SUMMARY OF THE INVENTION

The cultivar 'LIMteatime' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LIMteatime'. These characteristics in combination distinguish 'LIMteatime' as a new and distinct *Rosa* cultivar:

1. Clear pink petals.
2. High-centered blooms.
3. Continuous flowering.
4. Glossy foliage, resistant to blackspot and powdery mildew.
5. Plants can be grown on their own roots; grafting is not required.

PARENT COMPARISONS

Plants of the new cultivar 'LIMteatime' are similar to plants of the seed parent, in most horticultural characteristics, however, plants of the new cultivar 'LIMteatime' differ in the following:

1. Flower color of the new variety is pink, while the flower color of the seed parent is red.

Plants of the new cultivar 'LIMteatime' are similar to plants of the pollen parent in most horticultural characteristics, however, plants of the new cultivar 'LIMteatime' differs in the following:

1. Flower color of the new variety is more purple-pink, while the flower color of the pollen parent is more purple-red.
2. Flowers of the new variety produce about 70 petals, while flowers of the pollen parent produce about 30 petals.

COMMERCIAL COMPARISONS

Plants of the new cultivar 'LIMteatime' can be compared to the commercial variety *Rosa* 'Bucbi', U.S. Plant Pat. No. 4,225. These varieties are similar in most horticultural characteristics, however 'LIMteatime' differs in the following:

1. Flower color of the new variety is more purple-pink, while flower color of this comparator is more purple-red.
2. The new variety produces about 70 double petals, while this comparator produces about 20 semi-double petals.

3. Flowers of the new variety have a round to slightly irregular shape; flowers of this comparator have a cupped to flat shape.

Plants of the new cultivar 'LIMteatime' can also be compared to the commercial variety *Rosa* 'Belinda's Dream', unpatented. These varieties are similar in most horticultural characteristics, however 'LIMteatime' differs in the following:

1. Flowers of the new variety produce about 70 petals, while flowers of this comparator produce about 50 petals.

BRIEF DESCRIPTION OF THE PHOTOGRAPH

The accompanying photograph illustrates in full color a close up of an individual flower of 'LIMteatime'. The flower is approximately 4 days open from the bud stage and growing on a plant of about 18 months of age. The photograph was taken using conventional techniques and although colors may appear different from actual colors due to light reflectance it is as accurate as possible by conventional photographic techniques

DETAILED BOTANICAL DESCRIPTION

In the following description, color references are made to The Royal Horticultural Society Colour Chart 2007 except where general terms of ordinary dictionary significance are used. The following observations and measurements describe 'LIMteatime' plants grown outdoors, in Palm Desert, California. The growing temperature ranged from approximately 10° C. to 38° C. during the day and from approximately 5° C. to 22° C.during the night. Measurements were taken in September. General light conditions were very bright, normal sunlight. Measurements and numerical values represent averages of typical plant types.

Botanical classification: *Rosa* 'LIMteatime'.

Market classification: Floribunda rose.

PROPAGATION

Time to initiate roots: About 15 days at approximately 20° C.

Time to produce a rooted cutting: About 35 days at approximately 20° C.

PLANT

Age of plant described: Approximately 1.5 years.

Growth habit: Semi-upright, outwardly spreading.

Container size: 3-gallon.

Height: 60 cm.

Plant spread: 75 cm.

Rootstock: Own root.

Growth rate: Moderate.

Branching characteristics: Sympodial branching.

Length of primary lateral branches: Average range 18 to 35 cm.

Diameter of lateral branches: Approximately 6 mm to 7 mm.

Quantity of branches: 6 to 8 main branches, moderate lateral branches, 6 to 10 lateral branches per main branch.

Branches—young wood:

*Diameter*.—Approximately 4 mm.

*Texture*.—Glabrous, sparse minute, soft, short thorns.

*Approximate density/quantity of prickles*.—Sparse.

*Color*.—Near RHS Yellow-Green 152D. Faint flush Greyed-Red 181A.

Branches—old wood:

*Diameter*.—Approximately 5 to 9 mm.

*Color*.—Near RHS Green 137D.

*Texture*.—Glabrous. Oldest, basal growth scaly.

*Thorns*.—Approximate density/quantity of thorns: Young growth: Sparse to moderate, irregular occurring. Approximately 6 mm in diameter at base. 5 to 6 mm long. Colored near RHS Red-Purple 59C. Baase colored near Yellow-Green 151D. Not hooked. Mature growth: Moderately dense, apiculate thorns about 8 mm at base, 7 mm long. Colored near RHS Grey-Orange 165A, base colored near 165C. Not hooked.

FOLIAGE

Leaf:

*Arrangement*.—Alternate and compound.

*Quantity*.—Average 10 to 16 per main branch.

*Internode*.—Average range 3 cm to 6 cm.

*Average length*.—Approximately 12 to 13 cm.

*Average width*.—Approximately 8 cm.

Rachis:

*Average length*.—Approximately 5.5 cm.

*Average diameter*.—Approximately 2 mm.

*Color*.—Upper surface: Near RHS Yellow-Green 144C. Lower surface: Near RHS Yellow-Green 144B.

*Texture*.—Lightly prickled. Prickles colored near RHS Red-Purple 59C.

Leaflet:

*Quantity*.—5 or 7 per leaf, most commonly 5.

*Average length*.—Approximately 5.5 cm to 6.5 cm.

*Average width*.—Approximately 3.5 cm.

*Shape of blade*.—Broad ovate.

*Apex*.—Acute.

*Base*.—Broadly rounded.

*Margin*.—Finely serrate.

*Appearance of top surface*.—Slightly glossy.

*Appearance of bottom surface*.—Matte.

*Texture of top surface*.—Glabrous.

*Texture of bottom surface*.—Glabrous.

*Color*.—Young foliage upper side: Near RHS Green 139A. Very thin Greyed-Purple 187A on margin serrations. Young foliage under side: Near RHS Green 138B. Very thin Greyed-Purple 187A on margin serrations. Mature foliage upper side: Near RHS Green 137A. Very thin Greyed-Purple 187A on margin serrations. Mature foliage under side: Near RHS Green 138A. Very thin Greyed-Purple 187A on margin serrations.

*Venation*.—Type: Reticulate. Venation color upper side: Near RHS Yellow-Green 144C. Venation color under side: Near RHS Yellow-Green N144D.

Petiole:

*Average length*.—Approximately 3.0 cm to 4.0 cm.

*Average diameter*.—Approximately 3 mm.

*Texture*.—Glabrous.

*Color*.—Upper surface: Near RHS Yellow-Green 144C. Lower surface: Near RHS Yellow-Green 144B.

*Petiole wing*.—Typically 14 mm long and 5 mm wide. Apex apiculate. Upper surface colored near RHS Yellow-Green 144C, lower surface colored near Yellow-Green 145B. Texture: Glabrous.

FLOWER

Natural flowering season: Spring until Autumn.
Inflorescence type and habit: Singly occurring fully double rotate flowers.
Rate of flower opening: Approximately 8 days from bud to fully opened flower.
Flower longevity on plant: 10 to 14 days, after fully opened.
Quantity of flowers: 30 to 40 fully opened flowers and buds.
Flower size:
*Diameter*.—Approximately 9 cm to 10 cm.
*Height*.—Approximately 4 cm to 5 cm.
Flower shape:
*From above*.—Round to very slightly irregular round.
*Profile of upper part of flower*.—Flat.
*Profile of lower part of flower*.—Nearly flat, lower petals reflexing with age.
Peduncle:
*Length*.—4.0 cm to 5.5 cm.
*Diameter*.—4 mm.
*Color*.—Near RHS Yellow-Green 146C.
*Texture*.—Softly prickly.
Petals:
*Petal arrangement*.—Multiple rotate, overlapping whorls.
*Petal quantity*.—Average 70 to 85.
*Length*.—3.5 cm to 4.0 cm.
*Width*.—3.0 cm to 4.0 cm.
*Shape*.—Obovate.
*Margin*.—Entire.
*Apex*.—Rounded with 2 to 5 irregular shallow notches.
*Base*.—Very broad attenuate.
*Texture*.—Glabrous all surfaces.
*Color*.—When opening: Upper surface: Near RHS Red-Purple 68A. Small basal blotch White N155D flushed Yellow 3C. Lower surface: Near RHS Red-Purple 68B. Small basal blotch White N155D flushed Yellow 3C. Fully opened: Upper surface: Near RHS Red-Purple 73B flushed Purple 75C. Central petal section lightly streaked 65B. Very small basal blotch White N155D flushed Yellow 3D. Lower surface: Near RHS Red-Purple 73B flushed Purple 75C. Central petal section lightly streaked 65B. Very small basal blotch White N155D flushed Yellow 3D. Aging: Upper surface: Near RHS Red-Purple 73B flushed Purple 75C. Central petal section streaked 69B. Very small basal blotch White N155D flushed Yellow 3D. Lower surface: Near RHS Red-Purple 73B flushed Purple 75C. Central petal section streaked 69B. Very small basal blotch White N155D flushed Yellow 3D.
Bud:
*Shape*.—Ovate.
*Length*.—Approximately 3.5 cm.
*Diameter*.—Approximately 2.5 cm.
*Color*.—Near RHS Red-Purple 73A flushed 73C.
Sepals:
*Quantity*.—5.
*Length*.—2 cm.
*Width*.—9 mm.
*Shape*.—Deltoid.
*Apex*.—Acute. No sepal extensions.
*Margin*.—Entire.
*Texture*.—Slightly pubescent lower surface, densely and softly pubescent upper surface.
*Color*.—Interior Surface: Near RHS Green 138B. Exterior Surface: Near RHS Green 138A. Central blotch near Greyed-Purple 187B.
Receptacle:
*Height*.—5 mm.
*Diameter*.—10 mm.
*Shape*.—Flat.
*Color*.—Near RHS Yellow-Green 145C.
Fragrance: Strong lemony tea rose scent.

REPRODUCTIVE ORGANS

Stamens:
*Quantity*.—About 30.
*Filament length*.—Approximately 6 mm to 8 mm.
*Filament color*.—Near RHS Yellow-White 158B.
Anthers:
*Length*.—2 mm.
*Shape*.—Oblate.
*Color*.—Near RHS Greyed-Orange 167B.
*Pollen*.—None observed.
Pistil: Misshapen 3-parted structure in center of receptacle. About 4 mm in length and 3 mm in diameter. Colored near RHS Yellow-Green 145C.

OTHER CHARACTERISTICS

Seeds and fruits: Not observed.
Disease/pest resistance: Good overall disease resistance to normal pests and diseases typical of garden roses. Very good resistance to blackspot (*Diplocarpon rosae*) and powdery mildew (*Podosphaera pannosa*) disease.

What is claimed is:

1. A new and distinct cultivar of Floribunda Shrub Rose plant named 'LIMteatime' as herein illustrated and described.

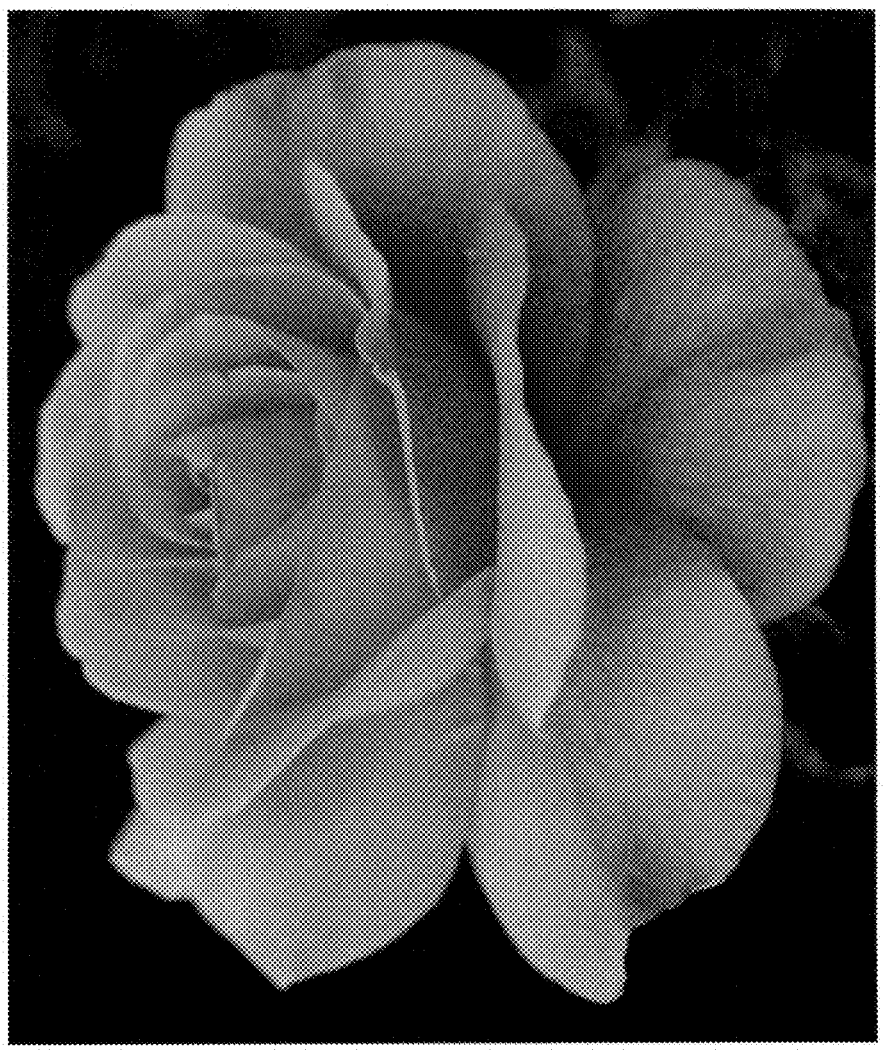

* * * * *